United States Patent
Landherr et al.

(10) Patent No.: US 12,318,618 B2
(45) Date of Patent: Jun. 3, 2025

(54) IMPLANTABLE MEDICAL DEVICE WITH FEEDTHROUGH ANTENNA GROUND STRUCTURE

(71) Applicant: CARDIAC PACEMAKERS, INC., St. Paul, MN (US)

(72) Inventors: Daniel Joseph Landherr, Wyoming, MN (US); Ron A. Balczewski, Bloomington, MN (US); Keith R. Maile, New Brighton, MN (US); Benjamin J. Haasl, Forest Lake, MN (US); Jason Lahr, Coon Rapids, MN (US); Niharika Varanasi, Shoreview, MN (US); Thao N. Nguyen, Lakeville, MN (US); Katherine Hauwiller, Plymouth, MN (US)

(73) Assignee: CARDIAC PACEMAKERS, INC.

( * ) Notice: Subject to any disclaimer, the term of this patent is extended or adjusted under 35 U.S.C. 154(b) by 545 days.

(21) Appl. No.: 17/695,599

(22) Filed: Mar. 15, 2022

(65) Prior Publication Data

US 2022/0288401 A1   Sep. 15, 2022

Related U.S. Application Data

(60) Provisional application No. 63/161,254, filed on Mar. 15, 2021.

(51) Int. Cl.
| | |
|---|---|
| *A61N 1/375* | (2006.01) |
| *A61N 1/372* | (2006.01) |
| *H01Q 1/27* | (2006.01) |
| *H04Q 9/00* | (2006.01) |

(52) U.S. Cl.
CPC ....... *A61N 1/37223* (2013.01); *A61N 1/3754* (2013.01); *H01Q 1/273* (2013.01); *H04Q 9/00* (2013.01); *H04Q 2209/43* (2013.01)

(58) Field of Classification Search
CPC .......................... A61N 1/3754; A61N 1/37223
See application file for complete search history.

(56) References Cited

U.S. PATENT DOCUMENTS

| | | |
|---|---|---|
| 6,031,710 A | 2/2000 | Wolf et al. |
| 2012/0109261 A1* | 5/2012 | Stancer ................ A61N 1/3718 607/60 |
| 2013/0235550 A1 | 9/2013 | Stevenson et al. |
| 2016/0151635 A1 | 6/2016 | Frysz et al. |
| 2019/0168005 A1 | 6/2019 | Li et al. |

(Continued)

*Primary Examiner* — George R Evanisko
(74) *Attorney, Agent, or Firm* — Seager, Tufte & Wickhem LLP

(57) ABSTRACT

An implantable medical device may include each of a conductive canister, a printed circuit board assembly (PCBA), and a header. A feedthrough and ferrule couple the interior of the canister, where the PCBA is, to one or more elements contained in the header such as an antenna and/or a port for coupling to a lead. The ferrule may be directly attached to the conductive canister and the electronic circuit board. The electronic circuit board carries an RF transmitter for telemetry purposes, and has an RF ground plane layer therein. The ferrule is capacitively coupled to the RF ground plane the PCBA, and has a size and/or shape relative to the RF ground plane that provides sufficient capacitance to offer an improved RF ground plane path to the conductive canister at a desired telemetry frequency.

10 Claims, 9 Drawing Sheets

(56) References Cited

U.S. PATENT DOCUMENTS

| | | |
|---|---|---|
| 2019/0321628 A1 | 10/2019 | Stevenson et al. |
| 2020/0054881 A1 | 2/2020 | Frustaci et al. |
| 2020/0246625 A1 | 8/2020 | Stevenson et al. |
| 2020/0276440 A1 | 9/2020 | Stevenson et al. |

* cited by examiner

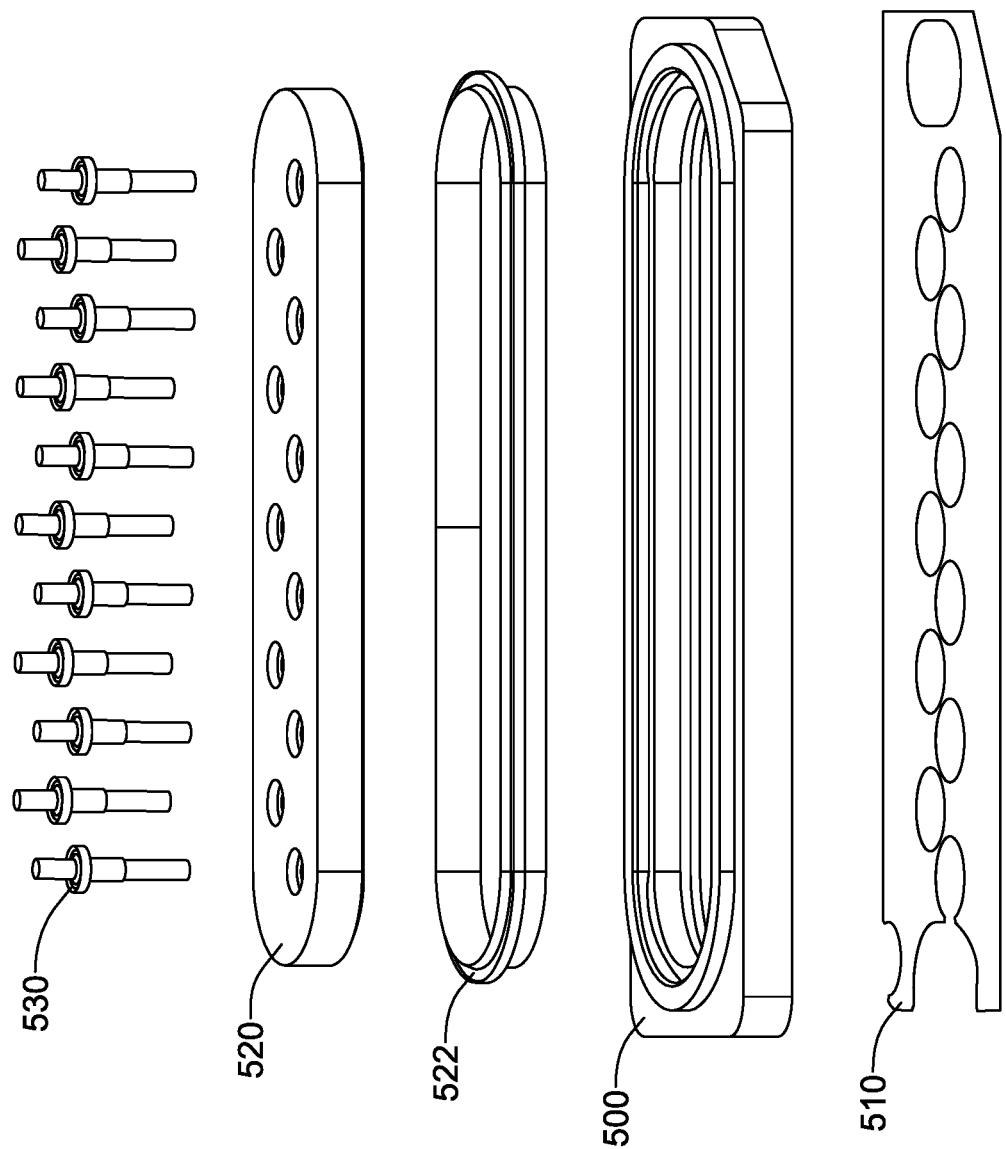

IMPLANTABLE MEDICAL DEVICE WITH FEEDTHROUGH ANTENNA GROUND STRUCTURE

CROSS REFERENCE TO RELATED APPLICATIONS

The present application claims the benefit of and priority to U.S. Provisional Patent Application No. 63/161,254, filed Mar. 15, 2021, titled IMPLANTABLE MEDICAL DEVICE WITH FEEDTHROUGH ANTENNA GROUND STRUCTURE, the disclosure of which is incorporated herein by reference.

BACKGROUND

Various implantable medical devices (IMDs) include telemetry circuitry and supporting software. The telemetry function is used to enable a user to control functions of the IMD, such as configuring therapy or turning therapy on and off, as well as allowing the user to monitor device status and load firmware upgrades to the device. For example, a pacemaker or defibrillator can be monitored to check battery status, device therapy history, and to obtain cardiac signal data recorded by the implantable device. Many implantable neuromodulation devices are configured with both clinician programmers and patient remote controls, allowing the physician to monitor and program the device, and allowing the patient to turn therapy on or off and/or make changes to therapy within limits programmed by their doctor.

Some early iterations of such devices relied on inductive telemetry, and more recent iterations have used RF telemetry. One example is the use of the Medradio (formerly the Medical Implant Communication Service or MICS) band in the region of 401-406 MHz. While earlier generations of these devices were used with specialized externals, custom made by the manufacturer of the IMD, the modern trend is to use off the shelf externals, such as tablet computers or even smart phones. The off the shelf devices, however, do not generally include, for example, Medradio-band telemetry circuitry. Bluetooth® and Bluetooth Low Energy (BLE) transmitters are commonly found in the off the shelf devices. The change to this higher frequency band (2.4 GHz) has led to reconsideration of hardware design of the IMD.

Overview

The present inventors have recognized, among other things, that a problem to be solved is the need for new and/or alternative designs to ensure adequate grounding of the RF telemetry circuit in an implantable medical device to the conductive can thereof.

A first illustrative and nonlimiting example takes the form of an implantable medical device (IMD) comprising: a conductive housing configured to provide an enclosure; circuitry disposed within the enclosure including at least a power source and a printed circuit board assembly (PCBA), the PCBA carrying at least an RF generator configured for use as a telemetry circuit for the IMD by operation within a communication frequency range, the PCBA including a first metallization layer therein, the first metallization layer comprising an RF portion serving as an RF ground plane for the RF generator, the RF generator having a direct electrical connection to the RF portion; a header coupled to the conductive housing; at least one feedthrough wire extending from the header into the enclosure of the conductive housing; and a ferrule surrounding the feedthrough, the ferrule coupled to the conductive housing; characterized in that: the ferrule is attached to the PCBA such that the ferrule is separated by a dielectric layer from the RF ground plane, thereby creating capacitive coupling between the ferrule and the RF ground plane, and the ferrule is sized and shaped to provide an impedance via the capacitive coupling of less than 3 ohms between the RF ground plane and the conductive housing within the communication frequency range.

Additionally or alternatively to the first illustrative and non-limiting example, the capacitive coupling of the ferrule to the RF ground plane provides a first connection of the RF ground plane to the conductive canister; the RF ground plane is capacitively coupled to a second metallization layer in the PCBA, and the second metallization layer is coupled by a wire to the conductive canister, thereby providing a second connection of the RF ground plane to the conductive canister; at DC the second connection has a lower impedance than the first connection; and in the communication frequency range, the first connection has a lower impedance than the second connection.

A second illustrative and non-limiting example takes the form of an implantable medical device (IMD) comprising: a conductive housing configured to provide an enclosure; circuitry disposed within the enclosure including at least a power source and a printed circuit board assembly (PCBA), the PCBA carrying at least an RF generator configured for use as a telemetry circuit for the IMD by operation within a communication frequency range, the PCBA including a first metallization layer therein, the first metallization layer comprising an RF portion serving as an RF ground plane for the RF generator, the RF generator having a direct electrical connection to the RF portion; a header coupled to the conductive housing; at least one feedthrough wire extending from the header into the enclosure of the conductive housing; and a ferrule surrounding the feedthrough, the ferrule coupled to the conductive housing; characterized in that: the ferrule is attached to the PCBA such that the ferrule is separated by a dielectric layer from the RF ground plane, thereby creating capacitive coupling between the ferrule and the RF ground plane; the capacitive coupling of the ferrule to the RF ground plane provides a first connection of the RF ground plane to the conductive canister; the RF ground plane is capacitively coupled to a second metallization layer in the PCBA, and the second metallization layer is coupled by a wire to the conductive canister, thereby providing a second connection of the RF ground plane to the conductive canister; at DC the second connection has a lower impedance than the first connection; and in the communication frequency range, the first connection has a lower impedance than the second connection.

Additionally or alternatively to the second illustrative, non-limiting example, the ferrule is sized and shaped to provide an impedance via the capacitive coupling of less than 3 ohms between the RF ground plane and the conductive housing within the communication frequency range.

Additionally or alternatively to either of the first or second illustrative, non-limiting examples, the communications frequency range is in the range of about 2.4 to 2.5 GHz.

Additionally or alternatively to either of the first or second illustrative, non-limiting examples, the communications frequency range is in the range of about 401 to 406 MHz.

Additionally or alternatively to either of the first or second illustrative, non-limiting examples, the communications frequency range is in the range of about 902-928 MHz.

Additionally or alternatively to either of the first or second illustrative, non-limiting examples, the communications frequency range is in the range of about 5.725 to 5.875 GHz.

Additionally or alternatively to either of the first or second illustrative, non-limiting examples, the ferrule and the RF portion are sized and shaped to provide an impedance of less than 2 ohms between the RF ground plane and the conductive housing within the communication frequency range.

Additionally or alternatively to either of the first or second illustrative, non-limiting examples, the ferrule and the RF portion are sized and shaped to provide an impedance of less than 1.5 ohms between the RF ground plane and the conductive housing within the communication frequency range.

Additionally or alternatively to either of the first or second illustrative, non-limiting examples, the ferrule defines a face that attaches to the PCBA, the face having an outer perimeter, and the RF portion has an outer perimeter corresponding to the outer perimeter of the face.

Another illustrative and non-limiting example takes the form of a method of generating an RF signal in an implantable medical device (IMD), the IMD including a conductive housing having an opening through which one or more feedthrough wires extend, the opening being sealed using a ferrule that resides in the opening, wherein the ferrule is mechanically coupled to both the housing and to a printed circuit board assembly (PCBA) carrying an RF generating circuit for the IMD; the method comprising: generating an RF output signal using the RF generating circuit; and grounding the RF generating circuit via capacitive coupling to the ferrule from a metallization layer in the PCBA and mechanical and electrical coupling of the ferrule to the conductive housing.

Additionally or alternatively, the step of grounding the RF generating circuit comprises encountering an impedance of less than three ohms while passing current through the capacitive coupling and the electrical coupling.

Additionally or alternatively, the step of grounding the RF generating circuit comprises encountering an impedance of less than two ohms while passing current through the capacitive coupling and the electrical coupling.

Additionally or alternatively, the step of generating an RF output signal comprises generating a frequency in the range of about 2.4 to 2.5 GHz.

Still another illustrative and non-limiting example takes the form of an implantable medical device (IMD) comprising: a conductive housing configured to provide an enclosure; circuitry disposed within the enclosure including at least a power source and a printed circuit board assembly (PCBA), the PCBA carrying at least an RF generator configured for use as a telemetry circuit for the IMD by operation within a communication frequency range, the PCBA including a first metallization layer therein, the first metallization layer comprising an RF portion serving as an RF ground plane for the RF generator, the RF generator having a direct electrical connection to the RF portion; a header coupled to the conductive housing; at least one feedthrough wire extending from the header into the enclosure of the conductive housing; and a ferrule surrounding the feedthrough, the ferrule coupled to the conductive housing, wherein the ferrule is attached to the PCBA such that the ferrule is separated by a dielectric layer from the RF ground plane, thereby creating capacitive coupling between the ferrule and the RF ground plane, and the ferrule is sized and shaped to provide an impedance via the capacitive coupling of less than 3 ohms between the RF ground plane and the conductive housing within the communication frequency range.

Additionally or alternatively, the capacitive coupling of the ferrule to the RF ground plane provides a first connection of the RF ground plane to the conductive canister; the RF ground plane is capacitively coupled to a second metallization layer in the PCBA, and the second metallization layer is coupled by a wire to the conductive canister, thereby providing a second connection of the RF ground plane to the conductive canister; at DC the second connection has a lower impedance than the first connection; and in the communication frequency range, the first connection has a lower impedance than the second connection.

Additionally or alternatively, the communications frequency range is in the range of about 2.4 to 2.5 GHz. Additionally or alternatively, wherein the communications frequency range is in the range of about 401 to 406 MHz. Additionally or alternatively, the communications frequency range is in the range of about 902-928 MHz. Additionally or alternatively, the communications frequency range is in the range of about 5.725 to 5.875 GHz.

Additionally or alternatively, the ferrule and the RF portion are sized and shaped to provide an impedance of less than 2 ohms between the RF ground plane and the conductive housing within the communication frequency range.

Additionally or alternatively, the ferrule and the RF portion are sized and shaped to provide an impedance of less than 1.5 ohms between the RF ground plane and the conductive housing within the communication frequency range.

Additionally or alternatively, the ferrule defines a face that attaches to the PCBA, the face having an outer perimeter, and the RF portion has an outer perimeter corresponding to the outer perimeter of the face.

Additionally or alternatively, the ferrule defines a face that attaches to the PCBA, the face having an outer perimeter within which the ferrule has one or more openings or gaps, and the RF portion has an outer perimeter corresponding to the outer perimeter of the ferrule face and one or more openings or gaps aligned with the one or more openings or gaps in the ferrule face.

Another illustrative and non-limiting example takes the form of a implantable medical device (IMD) comprising: a conductive housing configured to provide an enclosure; circuitry disposed within the enclosure including at least a power source and a printed circuit board assembly (PCBA), the PCBA carrying at least an RF generator configured for use as a telemetry circuit for the IMD by operation within a communication frequency range, the PCBA including a first metallization layer therein, the first metallization layer comprising an RF portion serving as an RF ground plane for the RF generator, the RF generator having a direct electrical connection to the RF portion; a header coupled to the conductive housing; at least one feedthrough wire extending from the header into the enclosure of the conductive housing; a ferrule surrounding the feedthrough, the ferrule coupled to the conductive housing; characterized in that: the ferrule is attached to the PCBA such that the ferrule is separated by a dielectric layer from the RF ground plane, thereby creating capacitive coupling between the ferrule and the RF ground plane; the capacitive coupling of the ferrule to the RF ground plane provides a first connection of the RF ground plane to the conductive canister; the RF ground plane is capacitively coupled to a second metallization layer in the PCBA, and the second metallization layer is coupled by a wire to the conductive canister, thereby providing a second connection of the RF ground plane to the conductive canister; at DC the second connection has a lower impedance than the first connection; and in the communication frequency range, the first connection has a lower impedance than the second connection.

Additionally or alternatively, the ferrule is sized and shaped to provide an impedance via the capacitive coupling of less than 3 ohms between the RF ground plane and the conductive housing within the communication frequency range.

Additionally or alternatively, the communications frequency range is in the range of about 2.4 to 2.5 GHz.

Additionally or alternatively, the ferrule and the RF portion are sized and shaped to provide an impedance of less than 2 ohms between the RF ground plane and the conductive housing within the communication frequency range.

Additionally or alternatively, the ferrule and the RF portion are sized and shaped to provide an impedance of less than 1.5 ohms between the RF ground plane and the conductive housing within the communication frequency range.

Additionally or alternatively, the ferrule defines a face that attaches to the PCBA, the face having an outer perimeter, and the RF portion has an outer perimeter corresponding to the outer perimeter of the face.

Another illustrative and non-limiting example takes the form of a method of generating an RF signal in an implantable medical device (IMD), the IMD including a conductive housing having an opening through which one or more feedthrough wires extend, the opening being sealed using a ferrule that resides in the opening, wherein the ferrule is mechanically coupled to both the housing and to a printed circuit board assembly (PCBA) carrying an RF generating circuit for the IMD; the method comprising: generating an RF output signal using the RF generating circuit; and grounding the RF generating circuit via capacitive coupling to the ferrule from a metallization layer in the PCBA and mechanical and electrical coupling of the ferrule to the conductive housing.

Additionally or alternatively, the step of grounding the RF generating circuit comprises encountering an impedance of less than three ohms while passing current through the capacitive coupling and the electrical coupling.

Additionally or alternatively, the step of grounding the RF generating circuit comprises encountering an impedance of less than two ohms while passing current through the capacitive coupling and the electrical coupling.

Additionally or alternatively, the step of generating an RF output signal comprises generating a frequency in the range of about 2.4 to 2.5 GHz.

This overview is intended to introduce the subject matter of the present application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7 is an exploded view of an illustrative feedthrough assembly.

DETAILED DESCRIPTION

A monopole antenna in an implantable medical device (IMD) typically uses the implantable device case as ground. Such an antenna would be used to communicate with the IMD using an external device such as a clinician or patient programmer to perform various diagnostic, configuration and control tasks. Because the IMD may be subjected to high voltages, such as when a defibrillation shock is externally applied or, in the event the IMD is a defibrillator, when the IMD itself issues a defibrillation shock, the electrical coupling of the case to the antenna and its signal generator is a capacitive connection. An ineffective electrical connection may significantly reduce telemetry capabilities.

Figure 1:
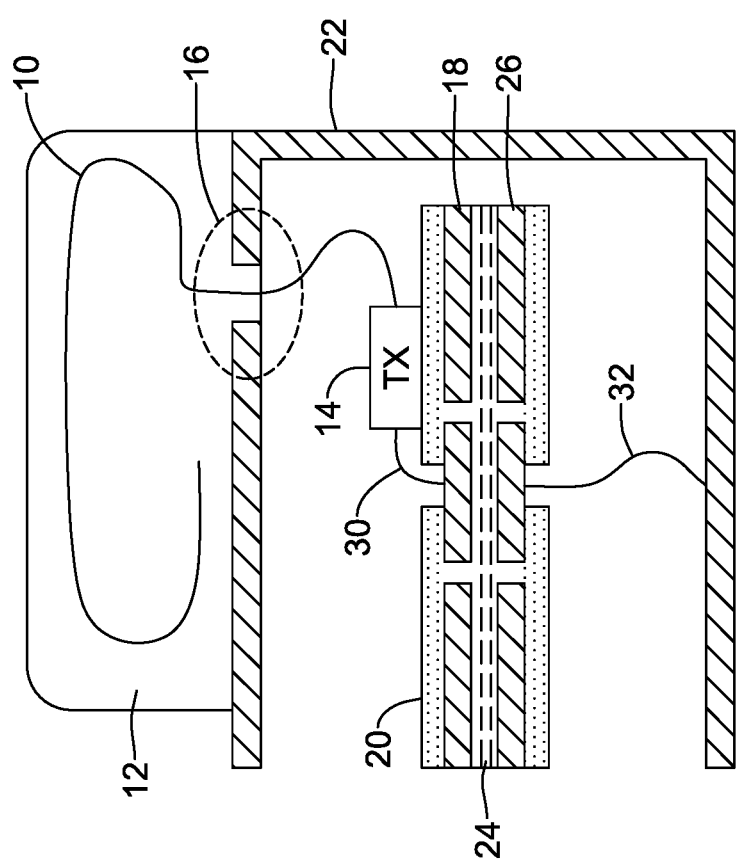
FIG. 1 schematically shows portions of an illustrative implantable medical device (IMD) in a partial section view.

FIG. 1 illustrates a prior design for supplying this capacitive connection. Here, the monopole antenna 10 resides mainly in the device header 12, which is shown in a simplified form with various other structures (such as a lead port and connections thereto) omitted for simplicity. The antenna 10 is electrically and mechanically linked to an RF generator 14 by passing through a feedthrough opening 16 into the canister. In other examples, the antenna 10 may be inside the canister 22, if desired, and/or there may be one or more additional wired connections passing through the feedthrough opening 16 to connect to a lead port or, in some examples, to an inductive loop used for recharging the device (as is commonly used in neuromodulation devices).

The RF generator 14 is electrically coupled to one of the metal layers 18 of a printed circuit board assembly (PCBA) 20 housed in the IMD case 22. The metal layer 18 resides on a substrate 24, and on the other side of the substrate is another metal layer 26, which is connected by a wire 32 to the IMD case 22. In this example, metal layer 26 may be the (battery negative) system ground. A capacitive coupling is used between the RF ground layer and the system ground layer to protect the RF circuitry 14 from therapy voltages if/when the conductive IPG case 22 is used as an electrode for therapy delivery purposes.

It may be noted that the drawings herein will illustrate highly simplified PCBA designs. It should be understood that implementation of a PCBA in an actual medical device may include plural additional alternating layers of dielectric/substrate and metallization, with as many as 4, 5, 6 or more metallization layers in some examples, with any number of components placed thereon.

At relatively lower frequencies, the parasitic inductance of the wire 32 is negligible enough to allow this circuit to function well for the RF ground. However, the current trend in IMD design is away from use of the Medradio frequency band (401-406 MHz), or even in some cases lower frequencies, to the use of Bluetooth at 2.4 GHz. With the higher frequency, the parasitic inductance coupling metal layer 26 via wire 28 to the IMD case 22 disrupts the ground connection, reducing the radiative power generated by the RF generator 14 and hampering telemetry overall. While one solution may be to use redundant or shorter wire connections at 28, still further alternatives are desired.

Figure 2:
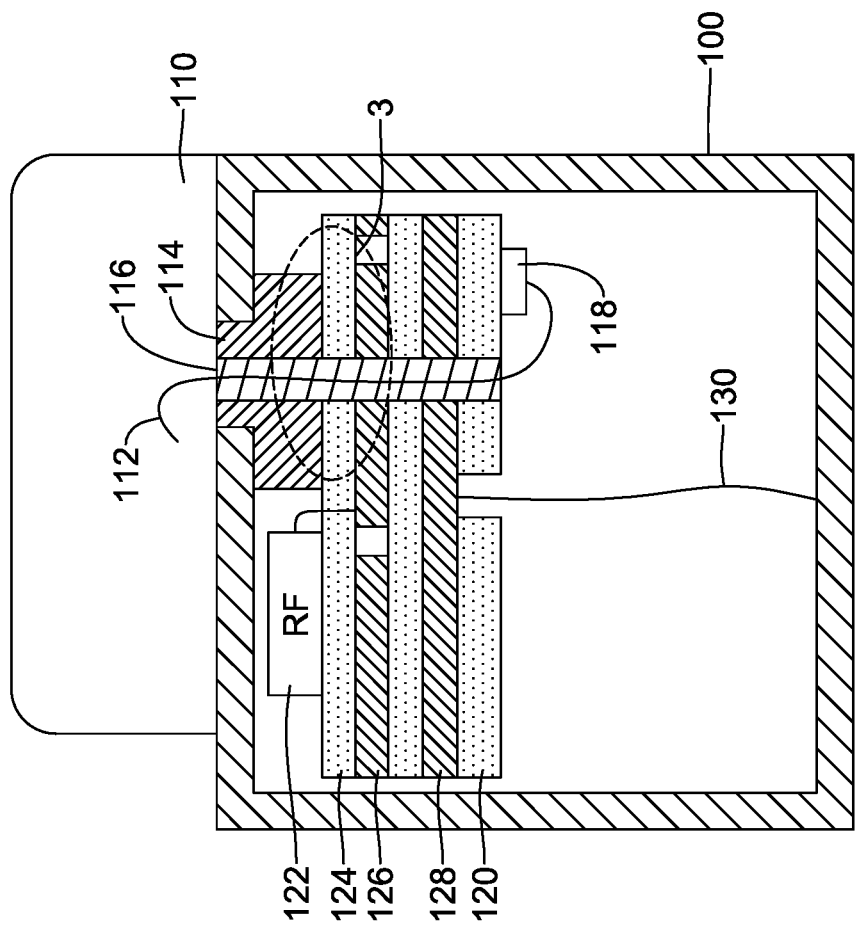
FIGS. 2-3 illustrate an illustrative example.
Figure 3:
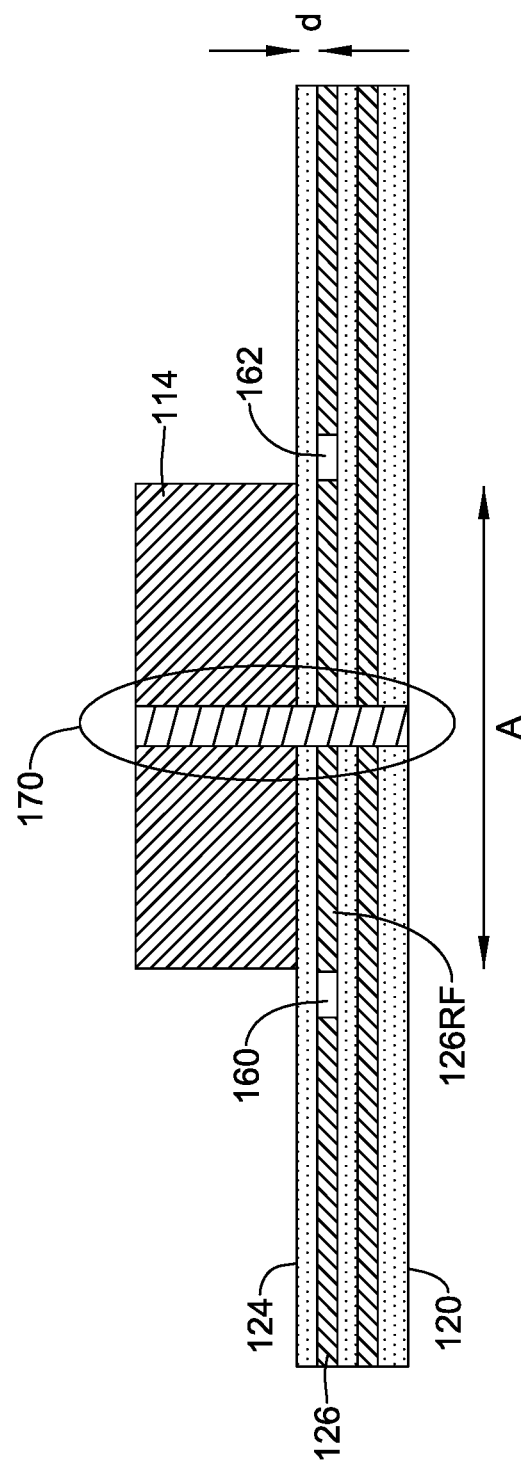

FIGS. 2-3 show an illustrative example. As shown in FIG. 2, the conductive housing 100 is mechanically fixed to a header 110 having at least one wire 112 extending therein. A feedthrough pin 116 extends through a dielectric within a ferrule 114 into the IPG through an opening in the conductive housing 100. The feedthrough pin 116 extends through the PCBA 120 to its bottom side, where a ribbon connection is provided to a capacitor 118 that can be used, as is known in the art, to filter incident energy such as from an MM, thereby protecting the device circuitry. The opening that the ferrule 114 is placed in may be a top opening or a side opening, as desired, in the IPG housing 100. A typical approach to the IPG housing is to use two clamshells that fit together, though some have proposed a deep drawn canister instead. For a clamshell design, the opening may be formed by each half of the clamshell, or the opening may be entirely defined by one of the two clamshells. In a deep drawn IPG housing, the opening may be part of the open end of the deep drawn housing, or it may be formed in a side or end thereof.

The ferrule 114 is directly attached by welding to the conductive housing 100, and is also mechanically attached to the top layer 124 of a PCBA 120 having therein a plurality of metallization layers 126, 128. As a result the ferrule 114 is both electrically connected and mechanically affixed to the conductive housing 100. In the example, an RF generator (sometimes referred to as an RF chip, an RF driver, an RF oscillator, etc.) 122 is wire connected to an RF portion of the metallization layer 126. In this example, the top metallization layer of the PCBA, that is, the one closest to the ferrule 114, has the RF portion, which serves as the RF ground layer.

In the illustration of FIG. 1, RF grounding is actually achieved by a combination of the capacitive coupling of layers 126 and 128, and a wired connection 130 to the conductive housing. In FIG. 2, however, the ferrule is sized and shaped to provide a separate capacitive coupling between the RF portion of layer 126 and the conductive canister 100. FIG. 3 provides a simplified view that adds to the illustration of the capacitive nature of the connection.

FIG. 3 is shown in different proportion than FIG. 2. The aspect and thickness ratios shown are not intended to exactly replicate what would actually be present in a system, but what is shown in FIG. 3 is somewhat closer to reality than FIG. 2. It can be seen that the RF portion of layer 126, designated as 126RF, is separated from the rest of layer 126 in this example by gaps 160, 162, using commonly known circuit board fabrication techniques. The capacitance between the ferrule 114 and the RF portion 126RF can be understood as approximating that of a parallel plate capacitor. Capacitance of a parallel plate capacitor is calculated as shown in Formula 1:

$$C = \varepsilon * \frac{A}{d} \quad \{\text{Formula 1}\}$$

Where $\varepsilon$ is the permittivity of the dielectric (that is, $K*\varepsilon_0$, where K is the relative dielectric constant and co is the dielectric constant, $8.9*10^{-12}$), A is the area of the parallel plates, and d is the distance between the parallel plates. For purposes herein, the approximation in Formula 1 is used, ignoring fringe effects for example.

In FIG. 3, the distance between the face of the ferrule 114 where it attaches to the top layer 124 of the PCBA 120, and layer 126 is indicated as d to the right side of the figure. The area A is as shown as well. Finally, the dielectric properties of the top layer 124 of the PCBA 120 is also used as shown in Formula 1. It should be understood in the preceding that "area" is not the same as the footprint taken by the ferrule 114 on the PCBA 120. "Area" is the surface area of the metal part of the ferrule that actually faces the PCBA over the RF ground layer 126RF. The footprint is the total surface area of the PCBA inside the outer perimeter of the face of the ferrule 114. Because there may be several through holes or other cut-outs, the footprint may be much larger than the area in this discussion. For example, the area consumed by the feedthrough at 170 would be subtracted.

The real component of impedance across a capacitor, as a function of frequency, shown in Formula 2:

$$Z = \frac{1}{2\pi FC} \quad \{\text{Formula 2}\}$$

Where F is the frequency, and C is the capacitance. Taking for example a Bluetooth frequency range as an example, the intended communication frequency range is about 2.4 to 2.485 GHz. For purposes herein it is sufficient to refer to the lowest frequency in the range (2.4 GHz for Bluetooth) because the impedances relevant to the following analysis drop as the frequency increases. While some references herein focus on Bluetooth, other communication frequency bands may be used as well, including, for example, the 5.725 to 5.875 GHz (ISM), and 902-928 MHz (ISM) bands, as well as the Medradio band, applying similar concepts to such bands. Any other suitable communication frequency and/or band may be used, as desired. Those skilled in the art will understand that both Formula 1 and Formula 2 are simplifications/approximations; each provides a sufficiently accurate approximation to be useful for the present discussion.

To obtain an impedance of about 5 ohms at the Bluetooth frequency, 13 picofarads of capacitance would be needed, and for 2 ohms, 33 picofarads. In illustrative examples, the capacitance is about 20 picofarads or more, or about 25 picofarads or more, or about 30 picofarads or more, or about 35 picofarads or more, or about 40 picofarads or more. Prior designs do not account for this use of the ferrule and would not have a ferrule size and shape large enough to achieve the level of capacitance discussed here. In particular, ferrule to RF ground plane capacitance greater than 20 pf does not appear to be known, let alone 25 pf or 30 pf.

Using Formula 1, and assuming a thickness of the dielectric of about 20 micrometers wherein the dielectric is FR4 (relative dielectric constant of about 3), one can extract the needed area of overlap between the RF portion of the metallization layer and the face of the ferrule. For 5 ohms, approximately 10.0 mm² of area is needed; for 2 ohms, about 25 mm² is needed. In illustrative examples, the impedance at a desired communication frequency may be 3 ohms or less, or 2.5 ohms or less, or 2 ohms or less, or 1.5 ohms or less, or 1 ohm or less, or 0.5 ohms or less.

To achieve a desired impedance at the communication frequency, the area in which the ferrule and the RF ground layer are capacitively coupled may be increased. Additionally or alternatively, higher capacitances and lower impedance in the desired communication frequency range can be further achieved with thinner dielectrics, for example, or by selecting a different dielectric to provide a larger dielectric constant, as desired. The following chart shows several examples at frequencies of 402 MHz (Medradio), 902 MHz (ISM), 2.4 GHz (Bluetooth), and 5.725 GHz (ISM):

| Z (Ohms) | F (GHz) | C (pf) | A (mm^2) |
|---|---|---|---|
| 5 | 0.4 | 79.6 | 59.9 |
| 3 | 0.4 | 132.6 | 99.9 |
| 2 | 0.4 | 198.9 | 149.8 |
| 1 | 0.4 | 397.9 | 299.6 |

-continued

| Z (Ohms) | F (GHz) | C (pf) | A (mm^2) |
|---|---|---|---|
| 5 | 0.9 | 35.4 | 26.6 |
| 3 | 0.9 | 58.9 | 44.4 |
| 2 | 0.9 | 88.4 | 66.6 |
| 1 | 0.9 | 176.8 | 133.2 |
| 5 | 2.4 | 13.3 | 10.0 |
| 3 | 2.4 | 22.1 | 16.6 |
| 2 | 2.4 | 33.2 | 25.0 |
| 1 | 2.4 | 66.3 | 49.9 |
| 5 | 5.7 | 5.6 | 4.2 |
| 3 | 5.7 | 9.3 | 7.0 |
| 2 | 5.7 | 14.0 | 10.5 |
| 1 | 5.7 | 27.9 | 21.0 |

Where the "impedance" is the real part of the impedance of the capacitive coupling at the given frequency, from which the capacitance and desired area are derived assuming a dielectric thickness of 20 micrometers, having a relative dielectric constant of 3. The skilled person will recognize that the other variables, including the dielectric thickness and dielectric constant, can be manipulated in addition to the area. While the above chart limits the examples to a range of 1 to 5 ohms, this are not intended to be limiting on the inventive concept. In some examples, it may be desirable to adjust the thickness of the dielectric and/or to select a specific dielectric to modify the needed area, as desired.

Figure 4A:
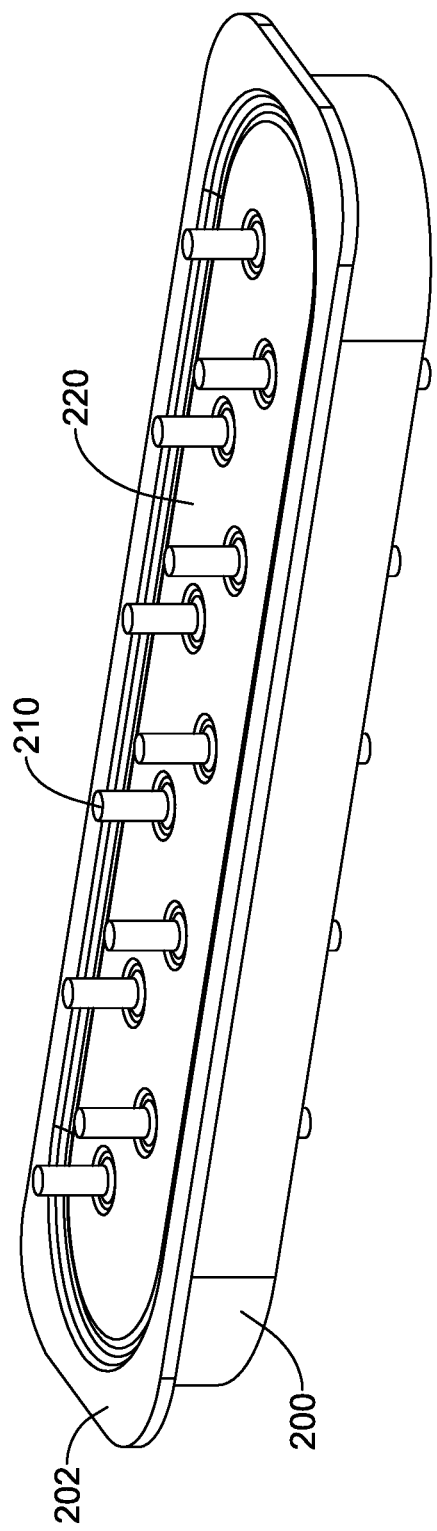
FIGS. 4A-4B, and 5A-5B show illustrative feedthrough assemblies with ferrules.
Figure 4B:
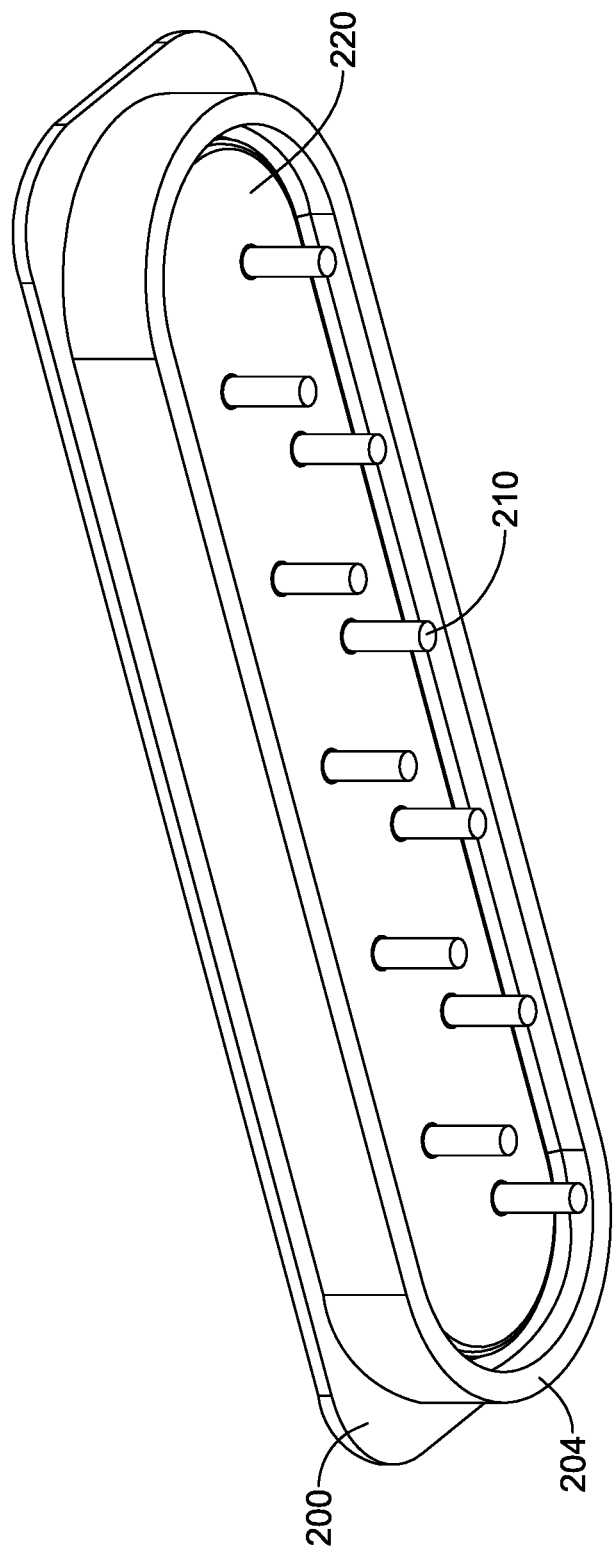

FIGS. 4A-4B, and 5A-5B show illustrative feedthrough assemblies with ferrules. FIG. 4A shows an upper perspective view of a feedthrough assembly including a ferrule 200 having an upper face 202 which would attach to the IPG canister itself. Feedthrough pins 210 extend through the interior of the ferrule 200 within a dielectric 220 that insulates the pins 210 from each other and from the ferrule 200. The bottom view of FIG. 4B shows that ferrule 200 also includes a bottom face 204 that would attach directly onto the top layer of the PCBA, with the pins 210 extending down through openings in the PCBA to the underside of the PCBA, as shown above in FIGS. 2-3. The wall of the ferrule 200 and face 204 in this example were built and found to be suboptimal for using a capacitive coupling to ground the RF circuit/antenna, as the area defined at face 204 did not provide sufficient area to achieve the desired capacitance and low impedance discussed above, at least in the context of a specific RF frequency band, dielectric type and dielectric thickness, as discussed above.

Figure 5A:
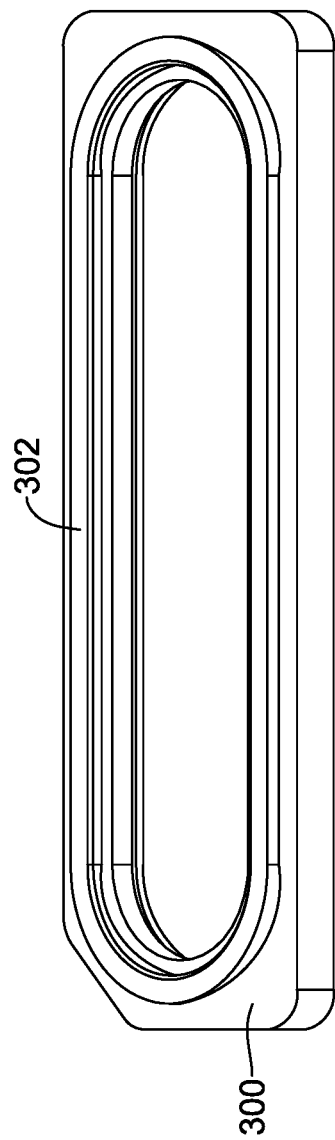
Figure 5B:
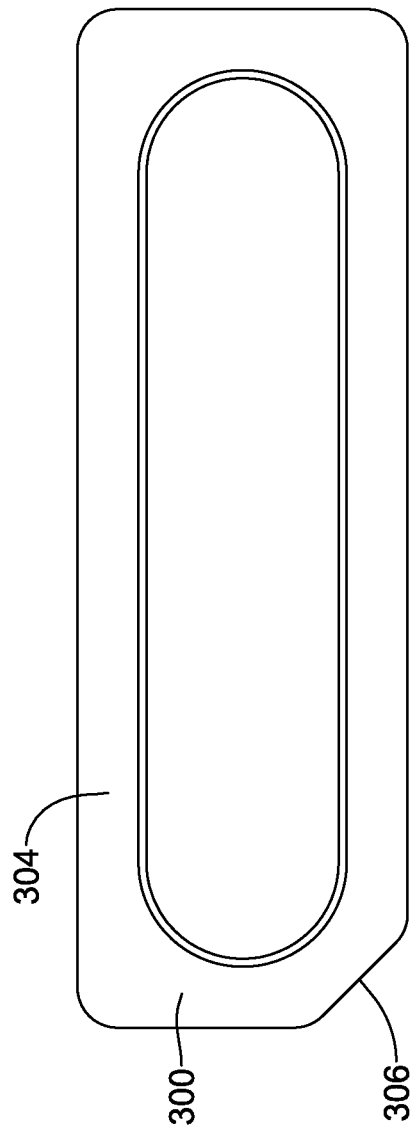

FIGS. 5A-5B show an enhancement relative to FIGS. 4A-4B. Here, the upper view in FIG. 5A shows a ferrule 300 having a top face 302 for welding to the IPG canister. The bottom view in FIG. 5B shows a larger face area 304 on ferrule 300. Optionally, to facilitate fit-up with other components, the face area 304 has a clipped corner 306 (not referring to the method of manufacture, but rather, the shape). Such shaping of the perimeter can be used to ensure appropriate fit-up with other components of the device as needed. This larger face area 304 was found to still further increase the capacitance and provided enhanced RF ground.

Figure 6:
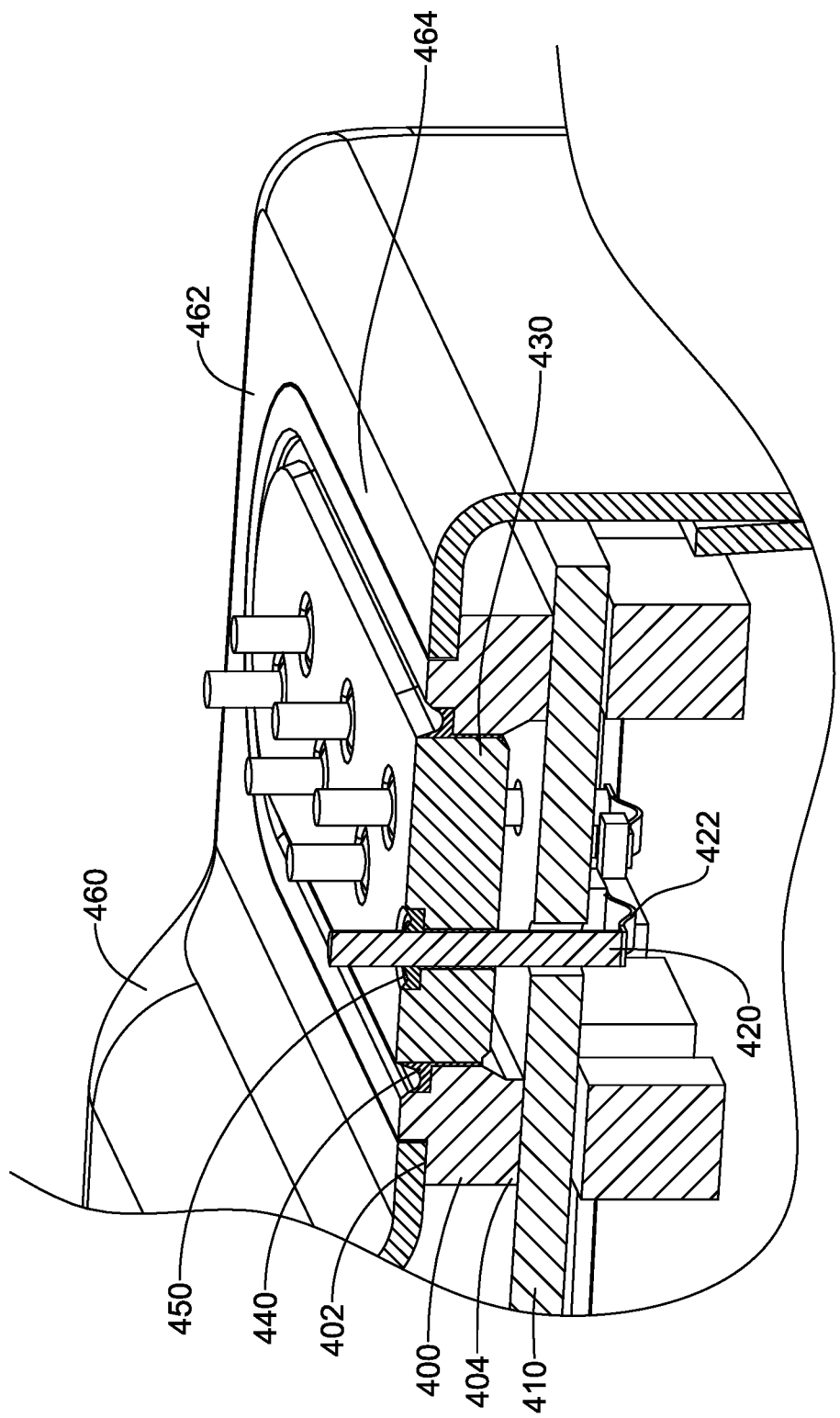
FIG. 6 shows an illustrative example in partial section view.

FIG. 6 shows an illustrative example in section view. Here, the ferrule 400 is shown in an opening 462 of the IPG canister 460. A first face of the ferrule at 402 is then welded to a portion 464 of the canister 460, which is shown having a recessed area in which the opening 462 resides.

The ferrule 400 also has a lower face 404 that is secured to the top layer (in some examples, a dielectric) of the PCBA 410. Feedthrough pins 420 extend through a dielectric 430 inside the ferrule 400. The feedthrough pins 420 and dielectric 430 may be placed by welding, adhesive or brazing, for example. For example, a preform ferrule braze 440 may be used to secure the dielectric 430 to the ferrule 400, and preform pin brazes 450 may be used to secure each pin 420 in its respective through-hold in the dielectric 430. Wire jumpers 422 then couple each pin to desired componentry on the PCBA 410; some feedthrough pins may couple to longer wires than that shown or may be directly coupled to layers in the PCBA 410 if desired. In some example, the upper face 402 that is welded to the IPG canister has a smaller surface area than the lower face 404 which is attached to the PCBA 410. Such relative sizing may be present in some examples; in other examples the two surface areas may be the same, or the surface area at 402 may be the larger of the two, if desired.

The IPG canister 460 would contain not only the PCBA 410 as shown, but may also contain additional components and/or circuitry as suit the use of the IPG. If, for example, the IPG is an implantable defibrillator, the IPG canister 460 may contain high power capacitors and charging circuitry (optionally, sometimes, on a separate PCBA or a "High Power Hybrid," as PCBA 410 may be the "Low Power Hybrid," as those terms are used in the art). For a cardiac pacemaker or neuromodulation device, the IPG may contain the PCBA as shown and one or more battery cells to power the device. For a rechargeable implanted device, such as certain neuromodulation devices, the IPG canister 460 may contain a charging circuitry and/or a charging coil for receiving power by inductive fields (a charging coil may instead be placed in the device header in which case one or more feedthrough pins 420 may couple to the charging coil).

Circuitry on the PCBA may include, for example and without limitation, control and logic circuitry such as a microcontroller, microprocessor, and/or state machine logic, as well as Flash or other memory circuitry, output circuitry for the issuance of therapy signals, gate array or other logic, analog and/or digital filtering circuitry, timers/oscillators, discrete logic and/or amplification devices, digital signal processing (DSP) chips, as well as application specific integrated circuits (ASICs) in any suitable combination. Any suitable combination of analog and/or digital control and logic circuitry, power source, and additional components specific to the function of the device may be considered "operational circuitry" of the IPG.

In an illustrative method, the PCBA 410 may carry RF circuitry, and, as shown, the housing 460 includes an opening 462 that is filled by the ferrule 430, with one or more feedthrough wires 420 passing therethrough. The ferrule 430 is mechanically and electrically coupled to the canister 460, and is also mechanically coupled to the PCBA 410, to create a capacitive coupling to a metallization layer in the PCBA 410. In the method, the RF circuitry is used to generate an output signal, and the method further includes grounding the RF circuitry during such generation of an output signal through the capacitive coupling and the electrical coupling of the ferrule 430. As used in the method, the "grounding" may be achieved if the electrical path defined by the ferrule electrical and capacitive coupling is the path of least resistance to ground at the communication frequency, which may be any desired frequency band, including those noted in particular examples above. Thus "grounding" may be achieved even if the electrical path defined via the ferrule is not the sole electrical path.

FIG. 7 is an exploded view of an illustrative feedthrough assembly. Here the ferrule 500 is configured to receive a ceramic feedthrough 520 with the aid of a braze element 522 that is used to create a brazed attachment therebetween. Feedthrough pins 530, each with their own braze elements, are shown as well. For illustrative purposes, the PCBA is omitted in the drawing with the exception of the RF portion 510 of the top metallization layer. As can be seen, the RF portion 510 generally matches the outer perimeter of the ferrule 500, while containing openings for each of the feedthrough pins.

The outer perimeters may be considered to "correspond" to one another if the outer of the two layers, as separated by a dielectric, line up to within less than two millimeter (mm) when viewed from "above" (in a downward direction as shown in FIG. 7) for at least 80% of the length of the perimeter. In the example shown in FIG. 7, the length and width of the RF portion 510 includes a cut-out at the end shown on the left, but otherwise has the same shape and dimensions (within one mm) as the outer perimeter of the ferrule 500. As a result, the example shown illustrates correspondence by having perimeters that are within one mm (closer than the two mm definition) for more than 90% of the perimeter (more than the 80% definition)—here, of approximately 45 mm outer perimeter on the ferrule, the outer perimeter of the RF portion 510 is within one mm for more than 41 mm.

The materials used throughout the design can include any suitable material known for use in the implantable medical device context. In some examples, the ferrule 500 may be formed of a Grade 2 titanium material. Titanium is one of several well-known materials that can be used for an IPG conductive housing.

Each of these non-limiting examples can stand on its own, or can be combined in various permutations or combinations with one or more of the other examples. The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. An implantable medical device (IMD) comprising:
a conductive housing configured to provide an enclosure;
circuitry disposed within the enclosure including at least a power source and a printed circuit board assembly (PCBA), the PCBA carrying at least an RF generator configured for use as a telemetry circuit for the IMD by operation within a communication frequency range, the PCBA including a first dielectric layer and a first metallization layer therein, the first metallization layer comprising an RF portion serving as an RF ground plane for the RF generator, the RF generator having a direct electrical connection to the RF portion;
a header coupled to the conductive housing;
at least one feedthrough wire extending from the header into the enclosure of the conductive housing; and
a ferrule surrounding the feedthrough, the ferrule coupled to the conductive housing, wherein the ferrule is attached to the PCBA such that the ferrule is separated by the first dielectric layer from the RF ground plane, thereby creating capacitive coupling between the ferrule and the RF ground plane, and the ferrule is sized and shaped to provide an impedance via the capacitive coupling of less than 3 ohms between the RF ground plane and the conductive housing within the communication frequency range.

2. The IMD of claim 1, wherein:
the capacitive coupling of the ferrule to the RF ground plane provides a first connection of the RF ground plane to the conductive housing;
the PCBA includes a second dielectric layer and a second metallization layer, the second metallization layer separated from the first metallization layer by the second dielectric layer;
the RF ground plane is capacitively coupled to the second metallization layer in the PCBA, and the second metallization layer is coupled by a wire to the conductive housing, thereby providing a second connection of the RF ground plane to the conductive housing;

at DC the second connection has a lower impedance than the first connection; and in the communication frequency range, the first connection has a lower impedance than the second connection.

3. The IMD of claim 1, wherein the communications frequency range is in the range of about 2.4 to 2.5 GHz.

4. The IMD of claim 1, wherein the communications frequency range is in the range of about 401 to 406 MHz.

5. The IMD of claim 1, wherein the communications frequency range is in the range of about 902-928 MHz.

6. The IMD of claim 1, wherein the communications frequency range is in the range of about 5.725 to 5.875 GHz.

7. The IMD of claim 1, wherein the ferrule and the RF portion are sized and shaped to provide an impedance of less than 2 ohms between the RF ground plane and the conductive housing within the communication frequency range.

8. The IMD of claim 1, wherein the ferrule and the RF portion are sized and shaped to provide an impedance of less than 1.5 ohms between the RF ground plane and the conductive housing within the communication frequency range.

9. The IMD of claim 1, wherein the ferrule defines a face that attaches to the PCBA, the face having an outer perimeter, and the RF portion has an outer perimeter corresponding to the outer perimeter of the face.

10. The IMD of claim 1, wherein the ferrule defines a face that attaches to the PCBA, the face having an outer perimeter within which the ferrule has one or more openings or gaps, and the RF portion has an outer perimeter corresponding to the outer perimeter of the ferrule face and one or more openings or gaps aligned with the one or more openings or gaps in the ferrule face.

\* \* \* \* \*